(12) United States Patent
Oosawa et al.

(10) Patent No.: US 10,685,412 B2
(45) Date of Patent: Jun. 16, 2020

(54) MEDICAL TEST RESULT DISPLAY DEVICE AND METHOD FOR OPERATING THE SAME

(71) Applicant: FUJIFILM CORPORATION, Tokyo (JP)

(72) Inventors: Akira Oosawa, Kanagawa (JP); Meiji Itoh, Kanagawa (JP); Yasunori Ohta, Kanagawa (JP); Shoji Kanada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1074 days.

(21) Appl. No.: 14/722,170

(22) Filed: May 27, 2015

(65) Prior Publication Data
US 2015/0254430 A1 Sep. 10, 2015

Related U.S. Application Data

(63) Continuation of application No. PCT/JP2013/081993, filed on Nov. 28, 2013.

(30) Foreign Application Priority Data

Nov. 30, 2012 (JP) .................................. 2012-262932

(51) Int. Cl.
*G06Q 50/00* (2012.01)
*G06Q 50/22* (2018.01)
(Continued)

(52) U.S. Cl.
CPC .............. *G06Q 50/22* (2013.01); *G06Q 50/24* (2013.01); *G16H 10/60* (2018.01); *G16H 15/00* (2018.01); *Y02A 90/22* (2018.01); *Y02A 90/26* (2018.01)

(58) Field of Classification Search
CPC .................................. G06F 19/00; G16H 10/60
(Continued)

(56) References Cited

U.S. PATENT DOCUMENTS 7,647,234 B1 * 1/2010 Ruderman .......... G06F 19/3418
705/2
8,315,883 B2 11/2012 Sakurai et al.
(Continued)

FOREIGN PATENT DOCUMENTS

| CN | 101169863 | 4/2008 |
|---|---|---|
| JP | 3408216 | 5/2003 |
| WO | 2012160796 | 11/2012 |

OTHER PUBLICATIONS

Mant, J., et al. "Systematic review and individual patient data meta-analysis of diagnosis of heart failure, with modelling of implications of different diagnostic strategies in primary care." NIHR Health Technology Assessment programme: Executive Summaries. NIHR Journals Library, 2009.*

(Continued)

*Primary Examiner* — Mark Holcomb
(74) *Attorney, Agent, or Firm* — JCIPRNET

(57) ABSTRACT

A medical test result display device and an operating method thereof are provided. An integration server reads out medical information from a medical case DB on the basis of a patient ID of a delivery request. A screen producing section reads out important test items from important test item information in accordance with an injury/disease code in the delivery request, and extracts test values on the important test items from the medical information. A case list creating section reads out representative case information from the medical case DB on the basis of the injury/disease code. The screen producing section produces a comparative display screen showing a test value graph based on the test values extracted from the medical information and a representative (Continued)

case graph based on test values in the representative case information in a manner allowing comparison therebetween, and delivers the screen to a department terminal to display same.

12 Claims, 16 Drawing Sheets

(51) Int. Cl.
    *G06Q 50/24*     (2012.01)
    *G16H 15/00*     (2018.01)
    *G16H 10/60*     (2018.01)

(58) Field of Classification Search
    USPC .......................................................... 705/2–4
    See application file for complete search history.

(56) References Cited

U.S. PATENT DOCUMENTS 9,122,773 B2     9/2015     Li et al.

2007/0088525 A1*   4/2007   Fotiades ........... G06F 17/30554
                                                                           702/131
2009/0030726 A1*   1/2009   Ortolani ................. G06Q 50/24
                                                                             705/3
2009/0292551 A1*  11/2009   Sirohey ................. G06F 19/321
                                                                             705/2
2010/0312798 A1*  12/2010   Dutta ...................... G16H 50/70
                                                                            707/780
2014/0122106 A1*   5/2014   Malven ............... G06F 19/3418
                                                                            705/2
2014/0324460 A1*  10/2014   Caffrey .............. G01N 33/6893
                                                                            705/3

OTHER PUBLICATIONS

"Office Action of China Counterpart Application," with English translation thereof, dated Apr. 27, 2017, p. 1-p. 17.

"Office Action of China Counterpart Application," with English translation thereof, dated Sep. 7, 2017, p. 1-p. 20.

* cited by examiner

FIG.5

MEDICAL RECORD DISPLAY SCREEN ( CASE COMPARISON DISPLAY )—62

BASIC PATIENT INFORMATION

| PATIENT ID AND PATIENT NAME | P1234 (ICHIRO FUJI) |
|---|---|

EXAMINATION RECORD

| CODE AND NAME OF INJURY/DISEASE | 013 (PNEUMOCOCCAL PNEUMONIA) |
|---|---|

TEST RESULT

| TEST CLASSIFICATION | TEST ITEM | DAY OF TEST | | |
|---|---|---|---|---|
| | | 2011/04/22 | 2011/04/25 | |
| VITAL | BT (°C) | 38.0 | 37.0 | |
| | SpO2 (%) | 92 | 95 | |
| BLOOD TEST | RBC (MILLION/μl) | 435 | 482 | |
| | WBC (NUMBER/μl) | 22100 | 5200 | |
| | Hb (g/dl) | 14.1 | 15.3 | |
| BIOCHEMICAL EXAMINATION | CRP (mg/dl) | 31.3 | 11.0 | |

TREATMENT RECORD

| TREATMENT CONTENTS | DAY OF TREATMENT |
|---|---|
| ABPC/SBT 6g | 2011/04/22 – 2011/04/25 |
| Oseltamivir 150mg | 2011/04/22 – 2011/04/25 |

FIG.6

| | | IMPORTANT TEST ITEM (54) | | | |
|---|---|---|---|---|---|
| TEST CLASSIFICATION | SMALL CLASSIFICATION | TEST ITEM | LIVER CANCER | PNEUMONIA | KIDNEY CANCER |
| VITAL | | BT (BODY TEMPERATURE) | ○ | ○ | ○ |
| | | SBP (SYSTOLIC BLOOD PRESSURE) | ○ | ○ | ○ |
| | | DBP (DIASTOLIC BLOOD PRESSURE) | ○ | ○ | ○ |
| | | PA (PULSE) | ○ | ○ | ○ |
| | | RRP (RESPIRATORY RATE) | ○ | ○ | ○ |
| | | WT (BODY WEIGHT) | ○ | | ○ |
| | | SpO2 (BLOOD OXYGEN SATURATION) | | ○ | |
| BLOOD TEST | GENERAL BLOOD TEST | PaO2 (ARTERIAL OXYGEN PARTIAL PRESSURE) | | ○ | |
| | | WBC (WHITE BLOOD CELL COUNT) | ○ | ○ | ○ |
| | | RBC (RED BLOOD CELL COUNT) | | | ○ |
| | | NEU (NEUTROPHILS) | | ○ | ○ |
| | | Lym (LYMPHOCYTES) | | ○ | |
| | | EOS (EOSINOPHILS) | | ○ | |
| | | Hb (HEMOGLOBIN CONCENTRATION) | | | ○ |
| | | Ht (HEMATOCRIT) | | | ○ |
| | | Plt (PLATELET COUNT) | | | ○ |
| | | ESR (ERYTHROCYTE SEDIMENTATION RATE) | | | ○ |
| | TUMOR MARKER | AFP (ALPHA-FETOPROTEIN) | ○ | | |
| | | AFP-L3 FRACTION | ○ | | |
| | | PIVKA-II | ○ | | |
| | | BFP (BASIC FETOPROTEIN) | | | ○ |
| BIOCHEMICAL EXAMINATION | INFLAMMATORY RESPONSE | CRP (C-REACTIVE PROTEIN) | ○ | ○ | ○ |
| | | AST(GOT) (GROUP TRANSFER ENZYME OF ASPARTIC ACID NETWORK) | ○ | | ○ |
| | | ALT (GPT) (ALANINE AMINOTRANSFERASE) | ○ | | ○ |
| | | Γ-GTP (GAMMA-GLUTAMYL -TRANSFERASE) | ○ | | |
| | | TP (SERUM TOTAL PROTEIN) | ○ | | |
| | | ALB (SERUM ALBUMIN) | ○ | | |

FIG.8

CASE LIST

SELECT REPRESENTATIVE CASE TO BE DISPLAYED ON COMPARATIVE DISPLAY SCREEN

REPRESENTATIVE CASE 1: PNEUMOCOCCAL PNEUMONIA (MILD)
REPRESENTATIVE CASE 2: PNEUMOCOCCAL PNEUMONIA (MODERATE)
REPRESENTATIVE CASE 3: PNEUMOCOCCAL PNEUMONIA (SEVERE)
REPRESENTATIVE CASE 4: PNEUMOCOCCAL PNEUMONIA (ULTRA-SEVERE)

ENTER

FIG.9

COMPARATIVE DISPLAY SCREEN

PATIENT TEST VALUE

2005　2006　2007　2008　2009　2010　2011　2012

| 2011/04/22 | 2011/04/25 |
| ABPC/SBT 6g |
| Oseltamivir 150mg |

WBC:22100
CRP:31.3
BT:38.0
SpO2:92

SpO2:95
CRP:11.0
BT:37.0
WBC:5200

REPRESENTATIVE CASES

2005　2006　2007　2008　2009　2010　2011　2012

| 2010/04/22 | 2010/04/25 | 2010/07/14 | 2010/07/21 |
| ABPC/SBT |
| Hydrocortisone |

WBC:21800　　WBC:22300　　SpO2:98　　　SpO2:98
CRP:29.8　　CRP:24.7　　　　　　　　WBC:17300
BT:38.5　　　　　　　　　　　CRP:2.7
　　　　　　　SpO2:92　　　　　　　　　BT:36.5
SpO2:82　　BT:36.9　　BT:36.9　　　　CRP:0.3
　　　　　　　　　　　　　　　　　　　WBC:6200

FIG.11

INPUT HISTORY ~56

| DATE AND TIME | USER ID | INJURY/DISEASE CODE | CASE ID |
|---|---|---|---|
| 2011/3/21 10:02 | 001 | 101 | AA01 |
| 2011/3/21 11:04 | 011 | 207 | BB02 |
| 2011/3/21 14:11 | 004 | 301 | CC11 |

FIG.12

RECOMMENDED CASE INFORMATION SCREEN ~90

USERS WHO CHECKED CASES
OF PNEUMOCOCCAL PNEUMONIA ALSO
REFERRED TO FOLLOWING CASE

~91

REPRESENTATIVE CASE AA

REPRESENTATIVE CASE AB

63

CONTENT DISPLAY ~92    ENTER ~93

MEDICAL TEST RESULT DISPLAY DEVICE AND METHOD FOR OPERATING THE SAME

CROSS-REFERENCE TO RELATED APPLICATIONS

This application is a Continuation of PCT International Application No. PCT/JP2013/081993 filed on Nov. 28, 2013, which claims priority under 35 U.S.C § 119 (a) to Japanese Patent Application No. 2012-262932 filed Nov. 30, 2012. The above application is hereby expressly incorporated by reference, in its entirety, into the present application.

BACKGROUND OF THE INVENTION

Field of the Invention

The present invention relates to a medical test result display device and a method for operating same.

Description Related to the Prior Art

In medical institutions, such as hospitals, computer systems are increasingly introduced for storing and managing medical information created during the medical practices on patients as electronic data, the medical information including medical examination records, medical treatment records, medical test results, etc. As one of these computer systems, a medical test result display device (hereinafter referred to simply as test result display device), which displays results of medical tests carried out on patients, has been known (refer to Japanese Patent No. 3408216).

Among many kinds of medical tests, some kinds, e.g., vital examination and blood test, include multiple test items in each test, and the test results of respective test items are expressed by numerical test values. As for a vital examination, the test items thereof may include pulse, blood pressure, body temperature, etc. As for a blood test, the test items thereof may include white blood cell count, red blood cell count, hemoglobin concentration in blood, etc.

A test result display device disclosed in Japanese Patent No. 3408216 has a capability of displaying test results of a plurality of tests which have been carried out at different time periods, in the form of time-series graphs of test values on individual test items. For instance, the test result display device creates a time-series graph of test values on each test item, such as pulse or blood pressure for the vital examination, or white blood cell count or red blood cell count for the blood test, and displays the graphs on a display screen. The time-series graph of test values shows a temporal change in test values, which facilitates recognizing the stage or extent of injury or disease in a patient and the therapeutic effects, such as the postoperative course and the reactions of medication, as well. Since the extent of injury or disease and the therapeutic effects provide important indicia for deciding therapeutic strategy, the time-series graph of test values is very useful.

In addition, the test result display device in Japanese Patent No. 3408216 displays an average range of test values on the same coordinate system as the time-series graph of test values is displayed. Thus, it is possible to check if each test value is normal or abnormal.

However, the test result display device in Japanese Patent No. 3408216 has a problem in that the operation thereof becomes cumbersome as the number of kinds of tests or test items increases, because of the following reasons. In general, medical practice are carried out in the following sequence. First, clinical examinations of a patient through interviews and the like are conducted to narrow down to a suspected injury or disease, and various kinds of tests are made on the patient in order to determine the injury or disease. From the comprehensive diagnoses based on the test results, the injury or disease is determined. After determining the injury or disease, a doctor decides on a therapeutic strategy on the basis of the test results, and provides medical treatments on the patient while repeating the medical tests to check the therapeutic effects.

When the doctor suspects a particular injury or disease, the doctor provides medical care focusing on particular important test items among multiple test items included in the test results from the patient. The important test items are those test items which the doctor must check up as particularly important items for the medical practice on the injury or disease. Since the important test items are different between different kinds of injuries and diseases, the important test items should be selected according to the injuries and diseases. Needless to say, the important test items change according to the kinds of medical tests. For example, from among multiple test items for a blood test, the doctor selects important test items according to the injury and disease, and checks the consequent test values. Likewise, if it is necessary to refer to test results of a vital examination in addition to the blood test, the doctor selects important test items from among multiple test items for the vital examination according to the injury or disease, and checks the consequent test values.

Thus, during the medical practice, multiple kinds of tests are repeated while making a selecting operation to select important test items according to the injury or disease from among multiple test items. The test result display device in Japanese Patent No. 3408216 is preferable as being capable of displaying the temporal alternation of test values. However, when many kinds of tests and test items should be selected, this device requires selecting important test items in a preparatory stage for displaying the test values, resulting in very poor operability.

When checking test results, it is general to check representative medical cases showing representative cases of other patients, including past test results thereof, in addition to test results of a patient as the subject of the medical practice. Comparing the test results on the patient with the representative cases is very useful for determining a therapeutic strategy or evaluating therapeutic effects. The test result display device in Japanese Patent No. 3408216 displays an average value range of the test values, but showing the average value range alone will not enable recognizing transitional changes of the test values in one representative case, for example, changes of test values before and after the treatment, and does not help evaluating the therapeutic effect.

For this reason, it is preferable to show the test values of the representative case in the form of a time-series graph, which, however, will require another selecting operation for selecting important test items to be displayed with respect to the representative case for each kind of injuries and diseases in addition to the test results on the patient, making the operation still more clumsy.

SUMMARY OF THE INVENTION

The present invention has an object to provide a medical test result display device and a method for operating same, which make it easy to check test values of important test items for individual injuries and diseases with respect to the test results on a patient and the representative cases as well without any cumbersome operation.

In order to solve the above problem, a medical test result display device in accordance with the present invention comprises an important test item memory section, a reception section, an important test item reading section, a test result obtaining section, a screen producing section and a display controller. The important test item memory section memorizes those test items to be referred to during the medical practice as important test items for each kind of injuries and diseases among multiple test items included in medical tests, of which test results are expressed by numerical test values. The reception section accepts an input of injury/disease identifying information for identifying each injury or disease. The important test item reading section reads out important test items corresponding to the received injury/disease identifying information from the important test item memory section. The test result obtaining section accesses both a test result storage and a representative case storage, to obtain test values on a patient as a present subject under medical practices and representative case information for comparison with the test values on the patient with respect to the important test items read out by the important test item reading section, wherein the test result storage stores test values of multiple test items included in medical tests carried out on the patient, and the representative case storage previously stores representative case information on each individual injury or disease, the representative case information indicating test values in representative medical cases. The screen producing section produces, on the basis of the obtained test values on the patient, a test value graph showing temporal change in test values of medical tests carried out on the patient a number of times at different time periods. The screen producing section also produces a representative case graph showing temporal change in test values in a representative medical case on the basis of the obtained representative case information, and produces a comparative display screen displaying the produced test value graph and the representative case graph in a manner allowing comparison therebetween. The display controller controls displaying the comparative display screen on a display device.

On the comparative display screen, the test value graph of the patient and the representative case graph are preferably displayed in a manner superposed on each other or in a manner apposed on each other. This will facilitate comparison between the test value graph and the representative case graph.

Preferably, the representative case information includes, in addition to the test values in representative medical cases, records on medical treatments performed in the individual medical cases, and the comparative display screen displays the medical treatment records in addition to the representative case graph. Thereby, it becomes easier to plan a therapeutic strategy on the basis of the medical treatment records.

Preferably, the medical test result display device of the present invention further includes a case list creating section that creates a case list of information on multiple representative cases stored in the representative case storage, wherein the display controller displays the case list on the display device, and the reception section accepts an input of case selecting information for selecting representative case information to be displayed on the comparative display screen from the case list. Thereby, it becomes possible to select representative case information according to the request of the user. Furthermore, displaying as a list makes it easier to select the representative case information.

Preferably, the representative case storage stores representative case information classified according to the kinds and severities of injuries and diseases, and the representative case list shows representative case information on one injury or disease classified according to the severity. Thereby, it becomes possible to select most suitable representative case information according to the severity, for use in comparison.

Preferably, the medical test result display device of the present invention further includes an input history recorder for recording input history information of individual users, which associates an input history of the injury/disease identifying information with an input history of the case selecting information, and an informing section for informing the user of such representative case information that other users have selected with respect to the same injury or disease on the basis of the input history information. Thereby, it becomes possible to recommend proven representative case information that has actually been utilized in medical fields.

The medical test result display device of the present invention further includes a case registration unit for registering representative medical cases in the representative case storage. Thereby, the usability of the representative case information will be improved, because it may, for example, be possible to register representative cases according the trend of medical practices in each medical facility.

Preferably, the medical test result display device of the present invention further includes a past case obtaining section that accesses a past case storage to obtain past case information, the past case storage storing past case information on multiple cases, indicating test values of past medical tests carried out on other patients than the patient as the present subject of the medical practice, wherein the case registration unit registers representative case information on the basis of the past case information obtained by the past case obtaining section. The case registration unit may register past case information selected from the obtained past case information as representative case information. Thereby, information on past cases of actually performed medical practices will be registered as representative case information, enabling to create representative case information suitable for actual medical practices.

The case registration unit preferably calculates representative values on the basis of test values included in the past case information on multiple cases, and registers the calculated representative value as representative case information. Thereby, more general representative cases will be available.

Preferably, the past case storage stores the past case information classified according to the kinds and severities of injuries and diseases, and the case registration unit registers representative case information classified according to the kinds and severities of injuries and diseases on the basis of the past case information. Thereby, it is possible to register most suitable representative case information according to the severity.

Preferably, the case registration unit is capable of receiving representative case information entered through a manual operation. Thereby, it becomes possible to employ common medical cases, such as those described in publications, as representative cases.

The medical test result display device of the present invention preferably includes an extracting section. When the test result obtaining section obtains representative case information on multiple cases, the extracting section extracts from among the representative case information on multiple cases, on the basis of a set of test values of medical tests carried out a number of times at different time periods in each case, such representative case information that contains a set of test values corresponding to a set of test values on the patient. Thereby, the representative case information on multiple cases can be narrowed down, making it possible even for unexperienced doctors to select representative case information without question. Furthermore, narrowing the range according to the similarity to the test values on the patient enables extracting such representative case information that is close in severity to the injury or disease of the patient even while the representative case information is not classified according to severities of injuries and diseases.

A method of operating a medical test result display device for displaying test results of medical tests in accordance with the present invention comprises an receiving step, an important test item reading step, a test result obtaining step, a screen producing step and a display control step. The receiving step is to accept an input of injury/disease identifying information for identifying each injury or disease. The important test item reading step is to read out important test items, which correspond to the injury/disease identifying information received at the receiving step, from an important test item memory section which memorizes test items to be referred to during the medical practice as important test items for individual kinds of injuries and diseases among multiple test items included in medical tests, of which test results are expressed by numerical test values. The test result obtaining step is to obtain, from among test values of multiple test items included in medical tests carried out on a patient as a present subject under medical practices and representative case information previously stored on each individual injury or disease and indicating test values in representative medical cases, those test values on the patient regarding the important test items read out in the important test item reading step and representative case information for use in comparison with these test values on the patient. The screen producing step produces, on the basis of the obtained test values on the patient, a test value graph showing temporal change in test values of medical tests carried out on the patient a number of times at different time periods. The screen producing step also produces a representative case graph showing temporal change in test values in a representative medical case on the basis of the obtained representative case information, and produces a comparative display screen displaying the produced test value graph and the representative case graph in a manner allowing comparison therebetween. The display control step is to control displaying the comparative display screen on a display device.

According to the present invention, important test items previously associated with individual kinds of injuries and diseases are read out, and test results on the patient and test values on representative cases are read out to be displayed with respect to the important test items. Therefore, it is unnecessary to make cumbersome selecting operation for selecting the important test items one by one, improving the operability. Thus, the present invention provides a medical test result display device and a method of operation therefor, which make it easy to check test values of important test items for individual injuries and diseases.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 5 is an explanatory diagram illustrating an example of a medical record display screen;

FIG. 6 is an explanatory diagram illustrating an example of important test item information expressed as a reference table;

FIG. 8 is an explanatory diagram illustrating an example of a case list;

FIG. 9 is an explanatory diagram illustrating an example of a comparative display screen;

FIG. 11 is an explanatory diagram illustrating an example of an input history;

FIG. 12 is an explanatory diagram illustrating an example of a recommended medical case noticing screen;

DESCRIPTION OF THE PREFERRED EMBODIMENTS

First Embodiment

Figure 1:
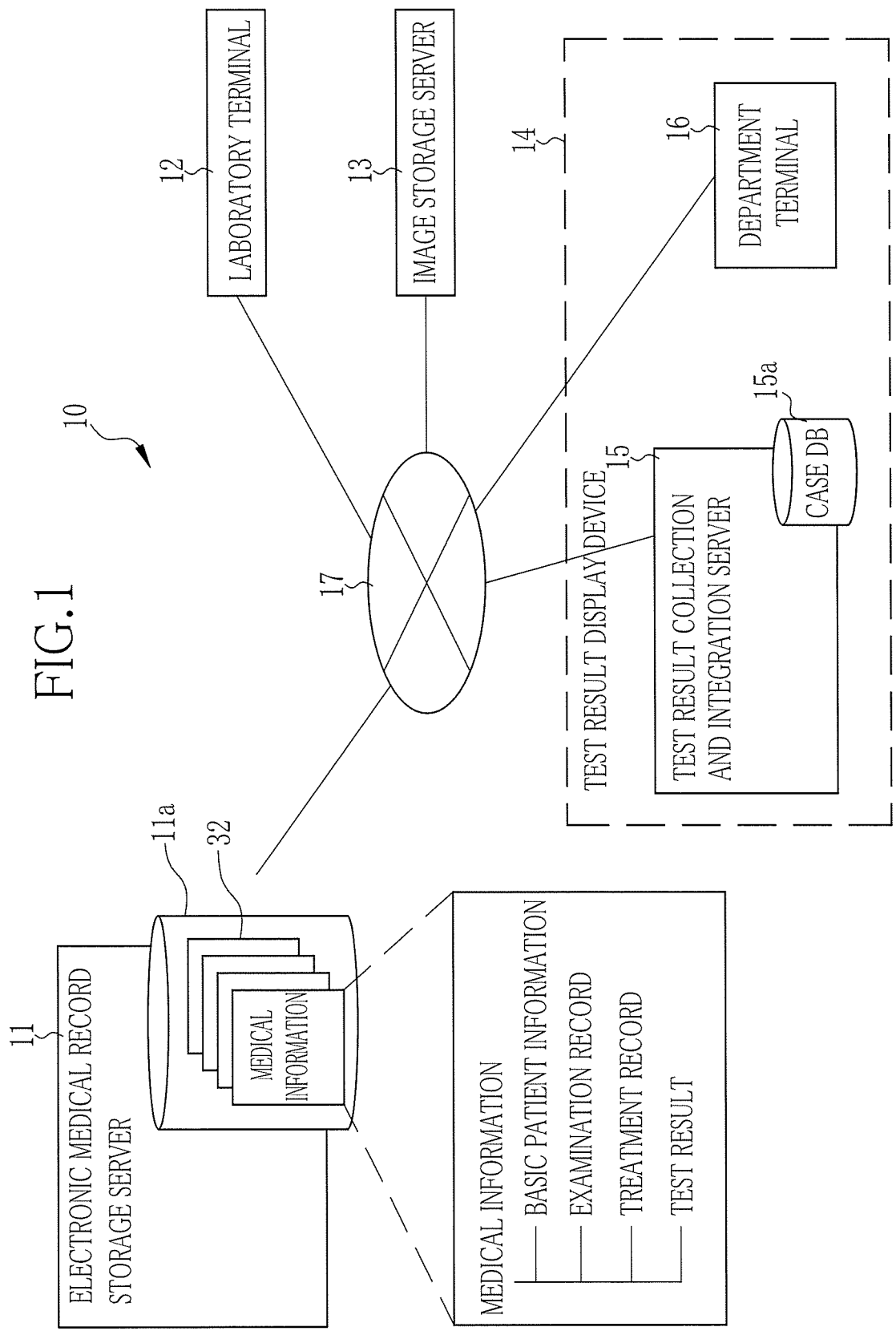
FIG. 1 is a schematic diagram illustrating a structure of a medical information system including a test result display device.

FIG. 1 shows a medical information system 10 that is a computer system serving for management of medical information in a medical facility such as a hospital. The medical information system 10 is constituted of an electronic medical record storage server 11 for storing and managing electronic medical records, a laboratory terminal 12 for inputting results of medical tests, an image storage server 13 for storing medical images, a test result display device (medical test result display device) 14 with a capability of displaying test results and cases in comparison with each other, and a network 17, such as LAN (local area network), connecting these components to enable communication therebetween.

The electronic medical record storage server 11 is provided with an electronic medical record database (hereinafter referred to as the medical record DB) 11a. The medical record DB 11a corresponds to the test result storage of the present invention. The medical record is recording medical information 32 on medical practices for each patient, and the medical information includes patient basic information, records of examinations and treatments carried out on the patient (examination records and treatment records), and test results of many kinds of medical tests carried out on the patient.

The patient basic information includes the name, birth date and sex of the patient, a patient ID, etc. The medical examination records include records of clinical interviews or palpations, etc., doctor findings, attended by injury/disease identifying information that includes an injury/disease name of a suspected or diagnosed injury or disease, and an injury/disease code for identifying the injury or disease. The injury/disease identifying information may include information on a plurality of injuries or diseases in a case where more than one injury or disease is suspected or involved.

The treatment records are records of operations, administrations and treatments carried out on the patient. As test results, results of medical tests expressed by numerical values, radiographic interpretation findings as results of imaging tests, and link information for the link to storage destinations of captured images (address information on storage destinations in the image storage server 13).

The medical tests, of which test results are expressed by numerical test values, include, for example, vital examinations, blood tests, biochemical examinations, urine tests and stool inspections. Each test includes multiple test items. For example, body temperature, blood pressure, pulse, respiratory rate, body weight, etc. may be cited as test items of a vital examination. As test items of a blood test, there may be white blood cell count, red blood cell count, hemoglobin concentration, etc. As test items of a biochemical examination, there may be protein, γ-GTP, etc. In the patient medical information 32, test values of these test items are recorded as test results along with the date of each test.

In general, when claiming an insurance, the injury/disease name and the injury/disease codes included in the medical information of an electronic medical record are often changed from an injury/disease name recorded by a doctor who diagnosed the injury or disease to a so-called receipt disease name, which is determined for the insurance claim on the basis of the contents of the medical practice, and a code corresponding to the receipt disease name. However, to avoid complicity of explanation, the present embodiments will be described on the premise that the injury/disease name and injury/disease code in the patient medical information 32 are not changed to the receipt disease name and the corresponding code.

Figure 2:
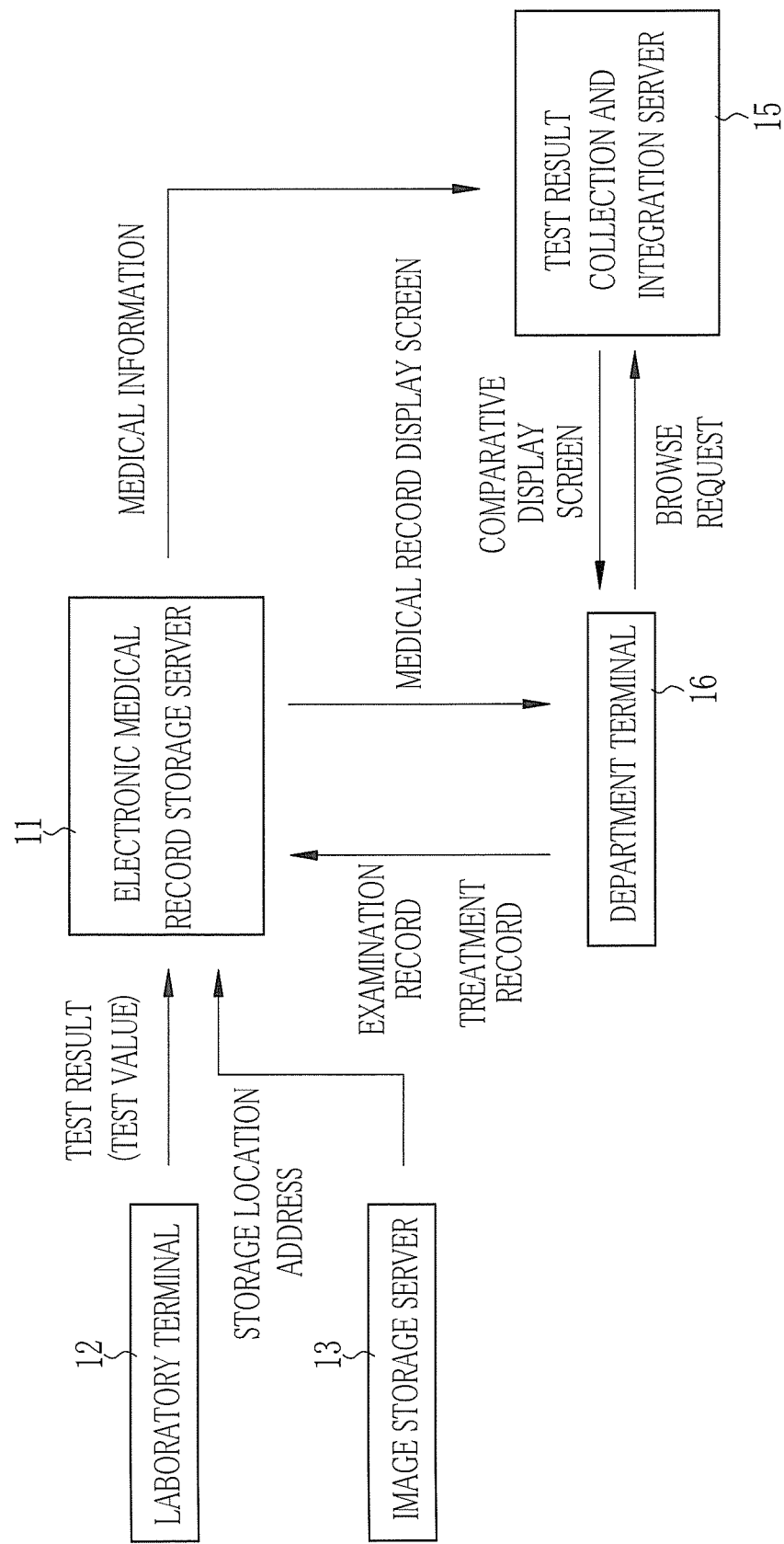
FIG. 2 is a schematic diagram illustrating major flows of information in the medical information system.

As shown in FIG. 2, the laboratory terminal 12 is installed in a laboratory for conducting blood tests, vital examinations, etc., and is used for registering test values in the electronic medical record storage server 11. The image storage server 13 is a server storing images captured for imaging tests. A storage location address of a captured image is sent from the image storage server 13 to the electronic medical record storage server 11, to be recorded as the medical information 32 therein.

In FIG. 1, the test result display device 14 is provided with a test result collection and integration server (hereinafter referred to as the integration server) 15 and a department terminal 16. The integration server 15 has a case database (DB) 15a for storing representative case information 51 (refer to FIG. 7) that indicates test values in representative cases for individual injuries/diseases and is used for comparison with test values on the patient. The case DB 15a corresponds to the representative case storage of the present invention. As shown in FIG. 2, the integration server 15 accesses the electronic medical record storage server 11 to collect the medical information 32 including test values, and has a capability of integrating the collected test values and the representative case information 51 obtained from the case DB 15a to produce a comparative display screen 71 (refer to FIG. 9) that displays the test values and the representative case information 51 in a manner allowing comparison therebetween. The integration server 15 produces the comparative display screen 71 upon receipt of a browse request, and delivers the produced comparative display screen 71 to the department terminal 16.

The department terminal 16 is a terminal installed in individual clinical departments, including those for internal medicine, surgery, otolaryngology and ophthalmology, and functions as a display terminal for displaying the comparative display screen 71 received from the integration server 15. The department terminal 16 also serves as a medical record terminal that accesses the electronic medical record storage server 11 to input examination records and treatment records therein or to receive a medical record display screen 61 (refer to FIG. 5) from the electronic medical record storage server 11, to display the medical information 32 for browsing.

The electronic medical record storage server 11, the laboratory terminal 12, the image storage server 13, the integration server 15 and the department terminal 16 are each configured on the basis of a computer, such as a personal computer, a server computer or a workstation, by installing a control program, such as an operating system, and an application program, such as a client program or a server program, therein.

Figure 3:
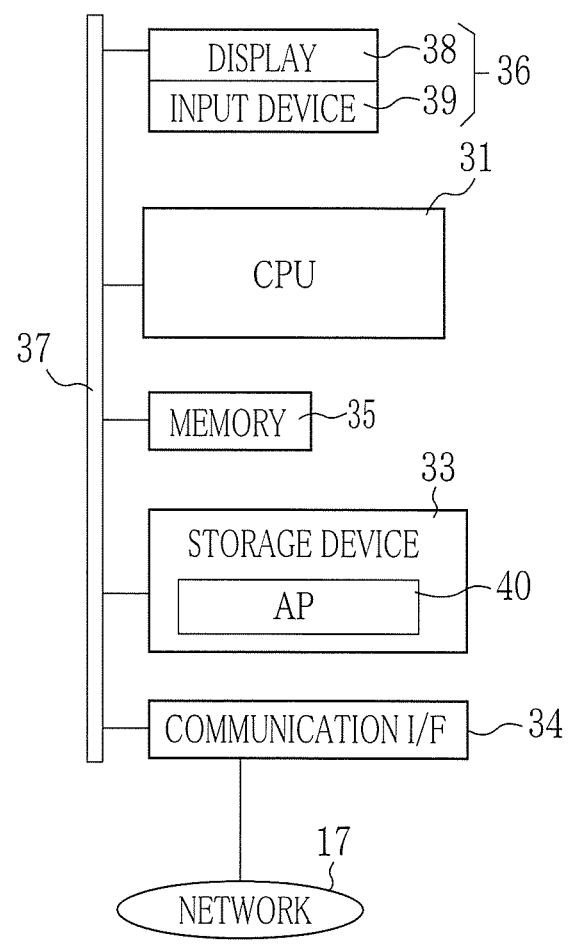
FIG. 3 is a block diagram illustrating an electrical structure of a computer serving as a test result display device and other devices.

As shown in FIG. 3, one computer is provided with a CPU 31, a memory 35, a storage device 33, a communication interface (I/F) 34 and a console 36. These components are interconnected through a data bus 37. The console 36 includes a display 38 and input devices 39, such as a keyboard and a mouse.

The storage device 33 is for example a hard disk drive (HDD) that stores the control program and the application program (AP) 40. In a computer for establishing a DB, a storage device 33 for the DB, for example, a disk array having an array of HDDs, is provided in addition to the HDD for storing the programs. The disk array may be integrated in the main body of the computer, or may be provided separately from the main body and connected to the main body through a cable or network.

The memory 35 is a work memory for the CPU 31 to execute processing. The CPU 31 loads the control program from the storage device 33 to the memory 35 and executes processing according to the program, controlling the components of the computer comprehensively. The communication I/F 34 is a network interface for controlling data transmission over the network 17.

The department terminal 16 is installed, as the AP 40, with client programs, such as software for medical records, enabling accessing the electronic medical record storage server 11 to browse or edit a medical record display screen 61 (refer to FIG. 5) that displays the medical information 32, and viewer software enabling accessing the integration server 15 or the image storage server 13 to browse a comparative display screen 71 (refer to FIG. 9) or images. The client program is a browser that receives screen data described in a markup language, e.g. extensible markup language (XML), and displays the screen on the display 38. The screen data includes operation screens based on graphical user interface (GUI).

Figure 4:
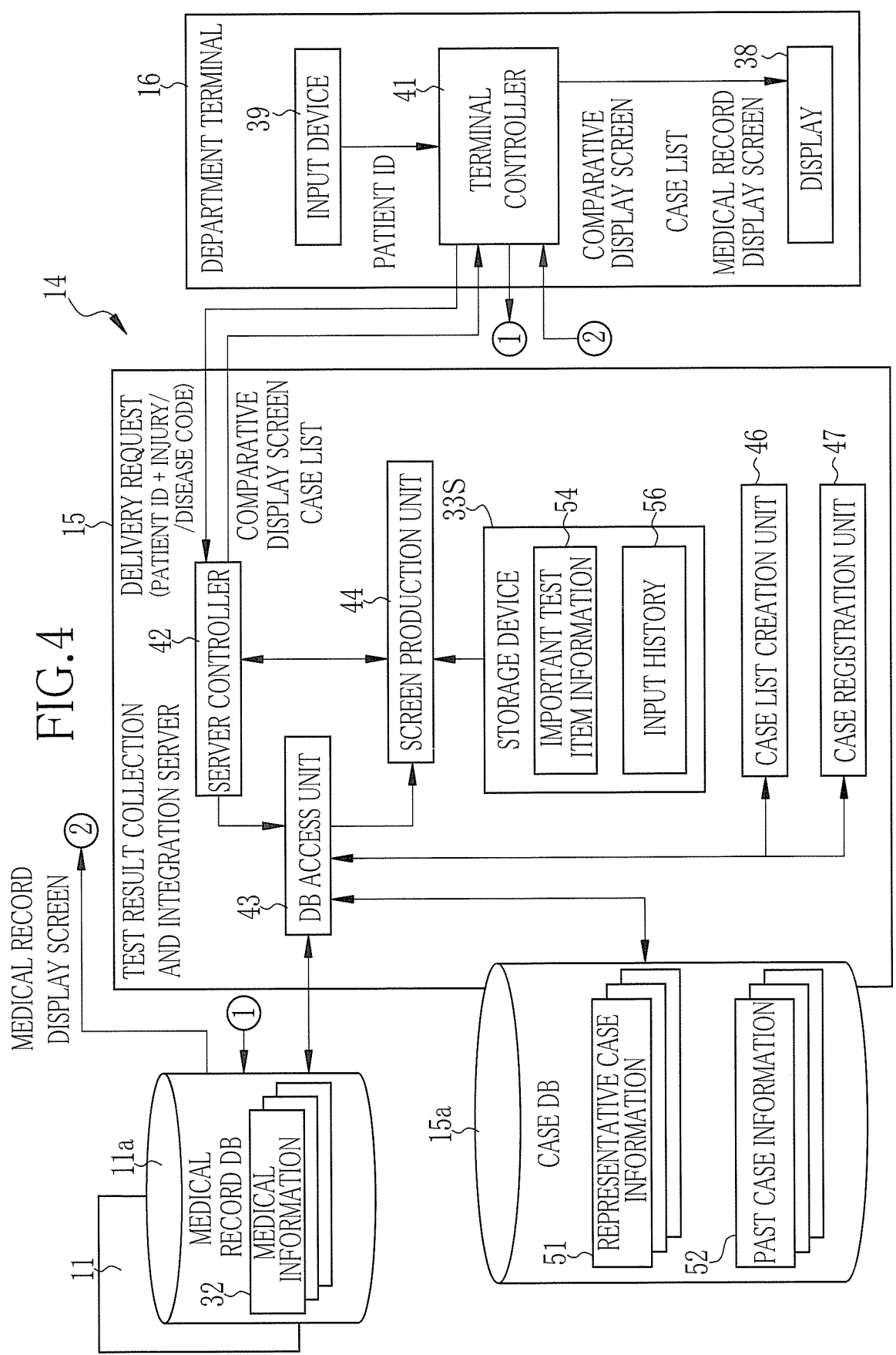
FIG. 4 is a block diagram illustrating a functional structure of test result display device.

As shown in FIG. 4, the CPU 31 of the department terminal 16 functions as a terminal controller 41 when the client program is executed. The terminal controller 41 accepts an input of information and various operation commands through the input device 39. When a patient ID is designated and a display command for displaying a medical record display screen 61 is received on the terminal controller 41, the terminal controller 41 sends a delivery request including the designated patient ID to the electronic medical record storage server 11 and receives the medical record display screen 61 corresponding to the designated patient ID. The terminal controller 41 functions also as the display controller of the present invention, controlling displaying the received medical record display screen 61 on the display 38.

As shown in FIG. 5, the medical record display screen 61 is provided with display columns for respectively displaying patient basic information, medical examination records, test results and treatment records included in the medical information 32. In the medical record display screen 61 of FIG. 5, the medical examination records involve, as disease identifying information, injury/disease name: "pneumococcal pneumonia", and a corresponding injury/disease code: "013". Entered as the test results are, for example, test values of test items of a vital examination, such as "body temperature (BT)", "blood oxygen saturation (SpO2)", and test values of test items of a blood test, such as "red blood cell count (RBC)", "white blood cell count (WBC)", "hemoglobin concentration (Hb)", test values of test items of a biochemical examination, such as "C-reactive protein (CRP)".

Although it is omitted from FIG. 5, it is assumed that the vital examination, the blood test, and the biochemical examination each include a lot of test items other than the test items shown in FIG. 5, and test values of many other test items are entered as the test results. In this example, respective kinds of tests have been carried out twice, and the individual dates of these tests are written with the test values. Entered as the treatment records are a therapeutic content that "6 g of a medical compound of ampicillin sodium and sodium sulbactam (ABPC/SBT)" and "150 mg of Oseltamivir" were administrated, and the dates of treatment, on which the medical treatment was provided. As the treatment dates, it is recorded that these medicines were administrated "from Apr. 22, 2011 to Apr. 25, 2011".

The medical record display screen 61 is provided with a case comparison display button 62 above the display columns for the medical information 32. The case comparison display button 62 is an operation button for instructing to display the comparative display screen 71 for the test values on the patient and the representative case information 51. When a mouse pointer 63 is operated to click on the case comparison display button 62 through the input device 39, a display command for the comparative display screen 71 enters the terminal controller 41.

The terminal controller 41 functions also as the reception section of the present invention and reads out, upon receipt of the display command for the comparative display screen 71, the patient ID ("P1234") and the injury/disease code ("013") from the medical information 32 displayed on the medical record display screen 61. The terminal controller 41 sends a delivery request, which includes the read patient ID and injury/disease code, to the integration server 15. The injury/disease code included in the delivery request corresponds to the injury/disease identifying information of the present invention. Note that the injury/disease name may be included in the delivery request in place of the injury/disease code. The terminal controller 41 receives the comparative display screen 71 in correspondence with the injury/disease code, and controls displaying the comparative display screen 71 on the display 38.

The integration server 15 is installed with a server program, as an AP 40, for executing processing in accordance with the request from the client. The CPU of the integration server 15 executes the server program to function as a server controller 42, a DB access unit 43, a screen production unit 44, a case list creation unit 46 and a case registration unit 47. The server controller 42 receives the delivery request form the department terminal 16 through the communication I/F 34, and controls the components of the integration server 15. The DB access unit 43 constitutes a part of the test result obtaining section of the present invention, and accesses the medical record DB 11a and the case DB 15a through the communication I/F 34, to obtain such patient medical information 32 and representative case information 51 that correspond to the patient ID and the injury/disease code included in the delivery request, respectively. The case DB 15a functions also as the past case storage of the present invention, storing past case information 52 that includes information on past cases for which medical practices have been finished, in addition to the representative case information 51. As set forth later, the past case information 51 is utilized as basic case information for the representative case information 51.

The case list creation unit 46 creates a case list 66 (refer to FIG. 8) that lists the multiple cases of the representative case information 51 stored in the case DB 15a. The case list 66 is sent to the department terminal 16 before the comparative display screen 71 being delivered, so that those representative cases to be displayed on the comparative display screen 71 may be selected from among the representative case information 51. The case registration unit 47 registers the representative case information 51 in the case DB 15a upon receipt of operation commands from the department terminal 16 and the console of the integration server 15.

The screen production unit 44 produces a comparative display screen 71 on the basis of the medical information 32 and the representative case information 51 obtained by the DB access unit 43, and delivers the produced comparative display screen 71 to the department terminal 16 through the server controller 42 and the communication I/F 34. In the integration server 15, a storage device 33S, which corresponds to the important test item storage and the input history recording section of the present invention, stores important test item information 54 and input histories 56. The input histories 56 include a history of delivery requests that the server controller 42 has received from the department terminals 16.

As shown in FIG. 6, in the important test item information 54, such test items that should be referred to during the medical practice are registered for each kind of injuries and diseases among a lot of test items included in a variety of medical tests, such as vital examination, blood test and biochemical examination. For example, the important test item information 54 is largely categorized by the kinds of medical tests, such as vital examination, blood test and biochemical examination, and test items involved in the individual kinds of medical tests are arranged in the subdivisions of each category. The names of injuries and diseases, such as lever cancer, pneumonia and kidney cancer, are arranged in a row. Although only the injury/disease names are shown in FIG. 6, the injury/disease codes are recorded in the important test item information 53 in addition to the injury/disease names.

In FIG. 6, marks "○" indicate important items for individual kinds of injuries and diseases. As important items for "pneumonia", items "SpO2", "Lym", "EOS", "CRP", etc. are marked with "○". The important items vary depending on the kinds of injuries and diseases. For instance, among test items of the blood test, the item "red blood cell count (RBC)" is not an important item for "pneumonia", but is regarded as an important item for "kidney cancer". The important test item information 54 is stored in the form of a reference table in the storage device 33S, which records important test items for the respective injuries and diseases in association with the individual injuries and diseases.

The important test item information 54 shown in FIG. 6 is just an example, wherein "lever cancer", "pneumonia" and "kidney cancer" are listed as the diseases, but in practice, "pneumonia" for instance is classified more finely according to the responsible microorganisms: "pneumococcal pneumonia", "Klebsiella Pneumoniae pneumonia", "influenza bacillus pneumonia", "Pseudomonas Aeruginosa pneumonia", "legionella pneumonia", etc. In the important test item information 54, important test items are recorded for each of the fine-classified injuries and diseases, specifically in a manner corresponding to the injury/disease identifying information which includes injury/disease names and injury/disease codes.

The important test item information 54 is provided, for example, as a content of the application program for the integration server 15, but may be newly created or updated in the medical facility. For this purpose, initially setup important items can be edited by the user so as to add or delete some items as needed. Since the decision on which test items are regarded as important among a plurality of test items can differ from doctor to doctor, the capability of editing the important test items enables the individual doctors to customize the important test items. The creation and revision of the important test item information 54 may for example be made on the console of the integration server 15 or the department terminal 16.

Figure 7:
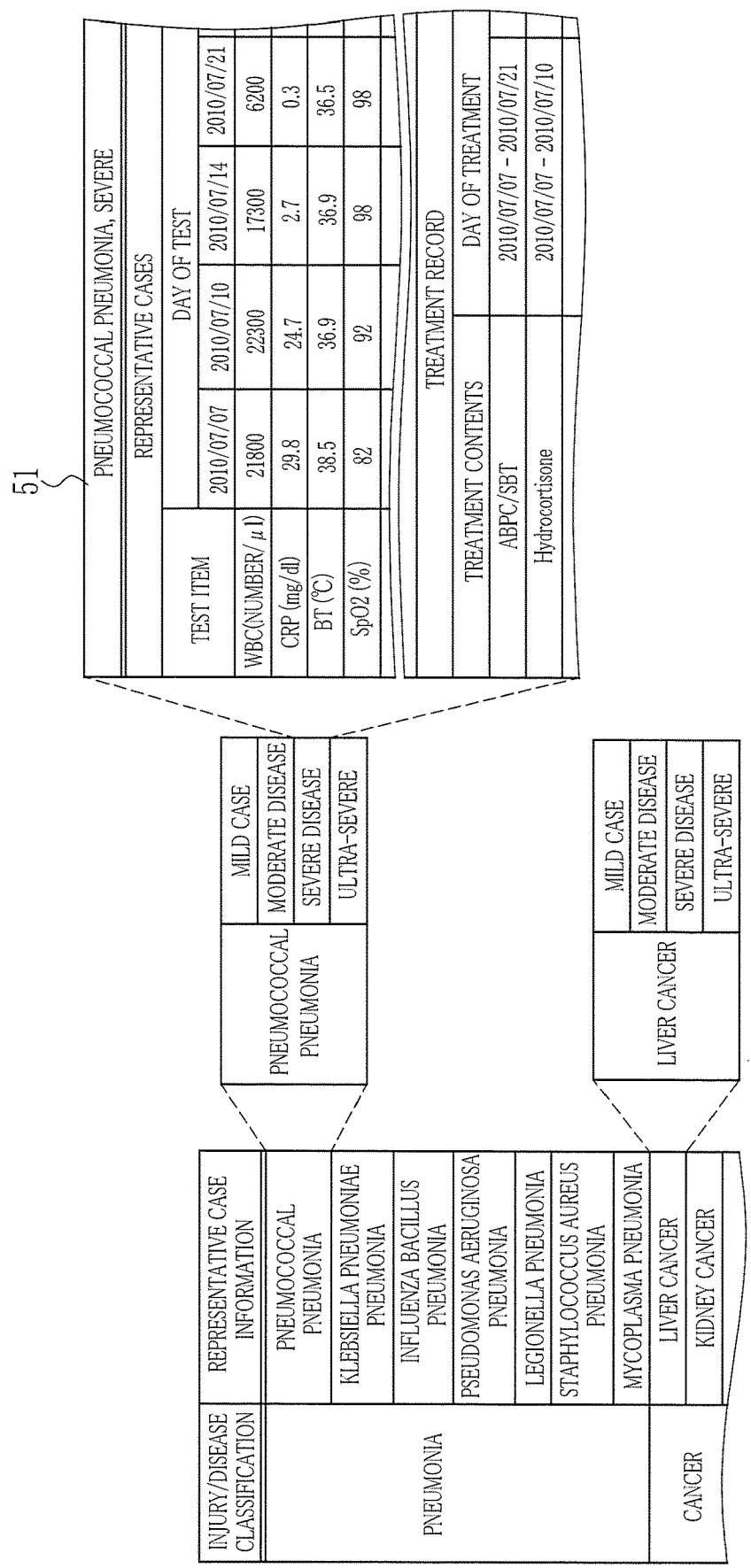
FIG. 7 is an explanatory diagram illustrating an example of representative case information.

As shown in FIG. 7, the case DB 15a stores the representative case information 51 for individual kinds of injuries and diseases. The representative case information 51 indicates test values obtained in representative medical cases for each kind of injury or disease. The test values included in the representative case information 51 correspond to test values of important test items which are determined by the kinds of injuries and diseases, and include those test values obtained by multiple medical tests conducted at different time periods. The representative case information 51 also includes, as treatment records, the contents of treatments, such as administration of medicines, along with the date when each treatment was applied. Accordingly, it is possible to grasp the change in test values before and after an administration in a representative case.

Also the injury/disease code for each injury/disease is recorded in the representative case information 51, so that the representative case information 51 may be retrieved on the basis of the injury/disease code. Furthermore, the stored representative case information 51 includes multiple cases for the same kind of injury or disease (e.g. "pneumococcal pneumonia"), which are classified according to the severities of symptoms of the injury or disease, e.g. "mild", "moderate", "severe" and "super-severe". Test values vary depending on the severity even for the same kind of injury or disease. Therefore, preparing the representative case information 51 for different levels of severity of each kind of injuries and diseases makes it possible to select a suitable case among the representative case information 51 according to the severity of injury or disease of the subject patient of the present medical practice. In addition, the representative case information 51 is recorded with a case ID for identifying each case of the representative case information 51.

As shown in FIG. 4, the case list creation unit 46 retrieves the representative case information 51 from the case DB 15a on the basis of the injury or disease code. If the representative case information 51 includes multiple cases for one injury or disease classified according to severity of the injury or disease, as illustrated in FIG. 7, all of the multiple cases in the representative case information 51 corresponding to the injury/disease code are extracted. Then, the case list creation unit 46 creates a case list 66 that lists the multiple cases of the representative case information 51 classified according to the severity. In an example shown in FIG. 8, the case list 66 lists multiple (four) cases of the representative case information 51 on "pneumococcal pneumonia" classified according to the severity. The case list 66 is delivered to the department terminal 16 through the server controller 42. The case list 66 is provided with an enter button 66a for confirming the selection. When the input device 39 is operated to select one case of the representative case information 51 and click on the enter button 66a by the mouse pointer 63 in the department terminal 16, the terminal controller 41 receives case selecting information. The case selecting information is sent from the department terminal 16 to the server controller 42.

Referring to FIG. 4, the screen production unit 44 functions also as an important test item reading section which accesses the storage device 33S to refer to the important test item information 54 and obtaining those important test items corresponding to the injury/disease code included in the delivery request. Furthermore, the screen production unit 44 cooperates with the DB access unit 43 to function as the test result obtaining section, extracting test values with respect to the obtained important test items from among test values of numbers of test items included in the medical information 32. The screen production unit 44 produces a comparative display screen 71 on the basis of the test values on the patient with respect to the extracted important test items and the representative case information 51 obtained by the DB access unit 43 and designated by the case selecting information.

As shown in FIG. 9, the comparative display screen 71 displays a test value graph 72 and a representative case graph 73 in a manner allowing comparison therebetween, wherein the test value graph 72 shows temporal change in test values of respective items on the basis of test values obtained from multiple tests carried out on the patient, whereas the representative case graph 73 are produced on the basis of the representative case information 51 to show temporal change in test values of a number of medical tests in a representative case. On each graph 72 or 73, the horizontal axis represents the time, and the vertical axis represents the magnitude of the test values. In the present example, the test value graph 72 is a time-series line graph that plots test values of two tests carried out on the patient on $22^{nd}$ and $25^{th}$ of April 2011 in chronological order and interconnects the test values with a line for each test item, whereas the representative case graph 73 is a time-series line graph that plots the test values of four tests carried out on $22^{nd}$ and $25^{th}$ of April 2010 and $14^{th}$ and $21^{st}$ of July 2010 in chronological order and interconnects the test values with a line for each test item. The test item and the numerical value are displayed beside each plot point. The date of execution of each test is displayed above the graphs 72 and 73.

The test value graph 72 and the representative case graph 73 respectively involve four test items: white blood cell count (WBC), C-reactive protein (CRP), body temperature (BT) and blood oxygen saturation (SpO2). The graphs 72 and 73 are equal in the kinds and the number of test items. Both of the graphs 72 and 73 merely display important test items determined according to the kind of injury/disease. Furthermore, on the graphs 72 and 73, the magnitude scales of the test values are standardized so as to penult grasping relative changes in the test values with respect to each test item, because the test values of different test items are expressed in different units from each other.

The comparative display screen 71 is provided with a first display field 74 for displaying the test value graph 72 and a second display field 75 for displaying the representative case graph 73, which are apposed on the upper and lower sides of the screen, respectively. The layout of the display fields are not limited to the illustrated example, but when the horizontal axes of the graphs 72 and 73 are assigned to be the time axes, it is preferable to employ the vertically divided screen layout so as to align the time scales.

Although the first display field 74 and the second display field 75 are apposed on the display screen 71, it is possible to display the graphs 72 and 73 in a superposed manner within a single display field. However, in a case where a lot of test items should be involved, the superposed display can lower the visibility, and therefore the apposed display like the present example is preferable. It is of course possible to make the display screen switchable between an apposed style and a superposed style. When displaying the graphs 72 and 73 superposed on each other, it is preferable to use different colors or types of lines and different colors, shapes or sizes of the plot points for discrimination between the individual test items in each of the graphs 72 and 73.

In either of the first and second display fields 74 and 75, a time period setup part 77 is provided for setting up the time of execution and the time range of medical tests of which test values are to be displayed. The time period setup part 77 is provided with a designation marker 77b slidable along a time axis 77a, and the length of the designation marker 77b in the axial direction is changeable. The designation marker 77b is operable through the input device 39. By sliding the designation marker 77b on the time axis 77a, a time period of medical tests is designated, and test values obtained in the designated time period are displayed as the test value graph 72 in the first display field 74 or the representative case graph 73 in the second display field 75. In FIG. 9, the first quarter of the year 2011 is designated as the time period of medical tests in the first display field 74, so that test values obtained from those medical tests carried out during the first quarter of the year 2011 are displayed as the test value graph 72.

As the axial length of the designation marker 77b being changed, the time range of the graph 72 or 73 will be changed. For example, when the length of the designation marker 77b designates one month, each of the graphs 72 and 73 will be displayed on the basis of test values of those medical tests which were carried out during one month. Note that, it may also be possible to adjust the scale on the time axis (e.g. the time interval between the tests) of each of the graphs 72 and 73.

Furthermore, in addition to the test value graph 72, treatment records 78 included in the medical information 32 are displayed in the first display field 74. In the second display field 75, treatment records 79 included in the representative case information 51 are displayed in addition to the representative case graph 73.

Figure 10:
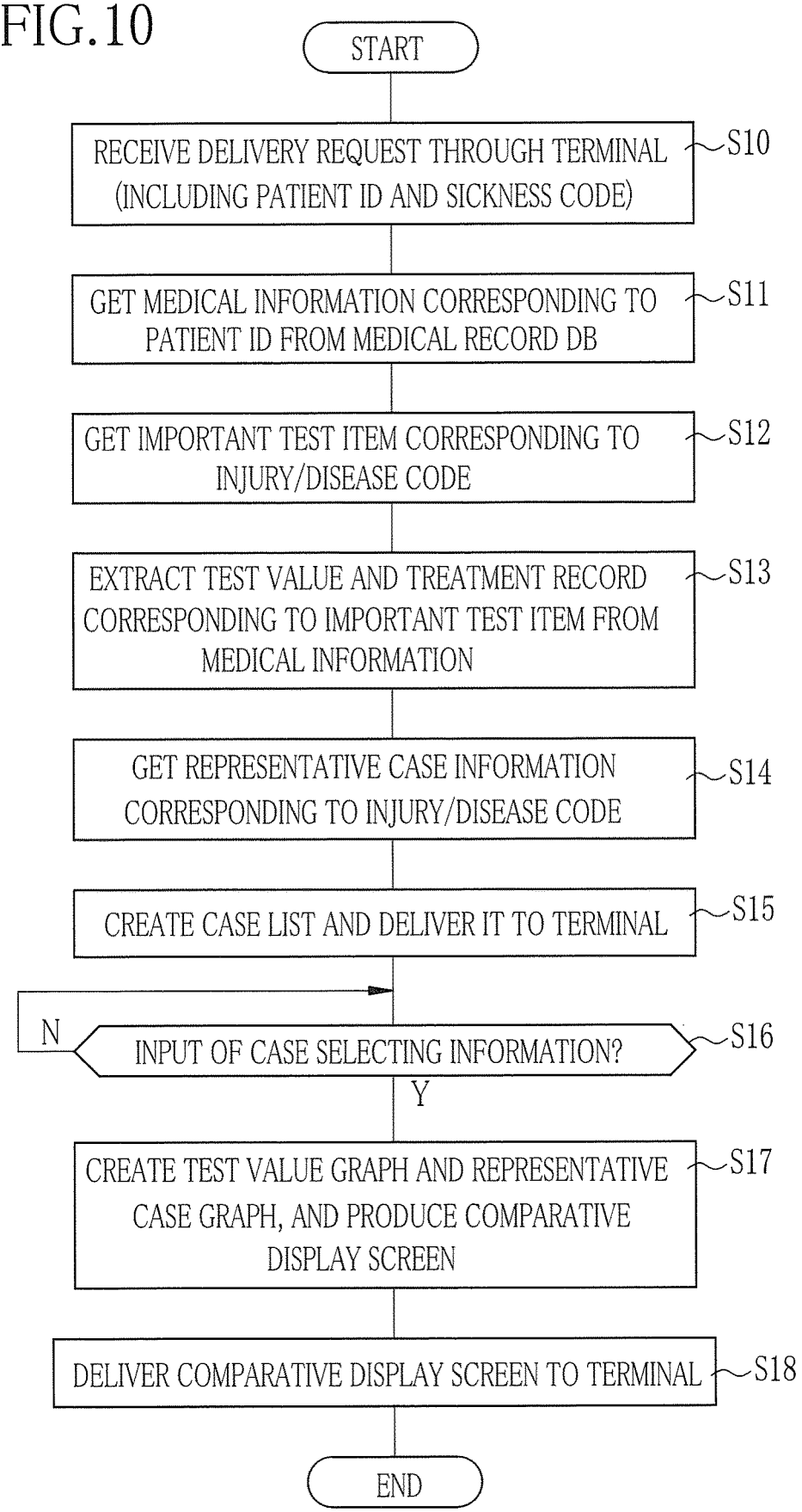
FIG. 10 is a flowchart illustrating a sequence of procedures for displaying the comparative display screen.

The operation of the above configuration will be described with reference to the flowchart shown in FIG. 10. When the terminal controller 41 accepts an input of a display command for the comparative display screen 71 on the medical record display screen 61, the terminal controller 41 reads out the patient ID ("P1234") and the injury/disease code ("013") from the medical information 32 displayed on the medical record display screen 61. The terminal controller 41 sends a delivery request, including the read patient ID and injury/disease code, to the integration server 15. The integration server 15 receives the delivery request from the department terminal 16 (S10).

The DB access unit 43 accesses the medical record DB 11a through the communication I/F 34, to obtain the medical information 32 corresponding to the patient ID included in the delivery request (S11). The screen production unit 44 accesses the storage device 33S, to refer to the important test item information 54 and obtain important test items corresponding to the injury/disease code included in the delivery request (S12). Then, from among the test values of a plurality of test items included in the medical information 32, test values of the obtained important test items are extracted (S13). In the example shown in FIG. 5, test values of "BT", "SpO2", "WBC", "CRP", etc. as important test items for "pneumococcal pneumonia" are extracted from test values on the respective test days included in the medical information 32.

The case list creation unit 46 access the case DB 15a through the DB access unit 43, to retrieve and obtain representative case information 51 on multiple cases of different severities from the case DB 15a on the basis of the injury/disease code (S14). The case list creation unit 46 creates a case list 66 that lists the obtained multiple cases of representative case information 51, and sends the case list 66 to the department terminal 16 (S15). The terminal controller 41 controls the display 38 to display the delivered case list 66. Thus, a doctor or a medical assistant can select one case of the representative case information 51 that is close in severity to the case of the patient under medical practice. In the department terminal 16, when the input device 39 is operated to select one case of the representative case information 51 and click on the enter button 66a by the mouse pointer 63, the terminal controller 41 receives case selecting information, the case selecting information is sent from the department terminal 16 to the server controller 42 (YES in S16).

The screen production unit 44 produces a comparative display screen 71 on the basis of the test values on the patient with respect to the extracted test items and the representative case information 51 obtained by the DB access unit 43 and designated by the case selecting information (S17). The screen production unit 44 delivers the produced comparative display screen 71 to the department terminal 16 through the server controller 42 and the communication I/F 34 (S18).

Upon receipt of the comparative display screen 71, the terminal controller 41 controls displaying the comparative display screen 71 on the display 38. The comparative display screen 71 displays a test value graph 72 and a representative case graph 73 in a manner allowing comparison therebetween, wherein the test value graph 72 shows temporal change in test values of respective items on the basis of test values obtained from multiple tests carried out on the patient, whereas the representative case graph 73 is produced on the basis of the representative case information 51 and show temporal change in test values of multiple tests in the representative case. In addition, treatment records 78 included in the medical information 32 are displayed in the first display field 74 for displaying the test value graph 72, whereas treatment records 79 included in the representative case information 51 are displayed in the second display field 75 for displaying the representative case graph 73.

The test value graph 72 and the representative case graph 73 are individually adjustable by operating the designation marker 77b of the time period setup part 77 with respect to the time period and time range in which the medical tests were executed. Furthermore, in the comparative display screen 71 shown in FIG. 9, the test value graph 72 and the representative case graph 73 are displayed such that respective periods of the tests from which the test values were obtained are adjusted on the time axes so as to correspond to each other between the test value graph 72 and the representative case graph 73, to thereby facilitate comparison therebetween. It may also be possible to display the date of beginning or the date of terminating the medical practice, etc. correspondingly between the test values on the patient and the representative case.

According to the present embodiment, when a command for displaying the comparative display screen 71 is entered on the medical record display screen 61, the injury/disease code is read out from the medical information 32 of the patient, and the important test items allocated to each individual injury or disease. Then, those test values regarding the important test items are extracted to be displayed as the test value graph 72. Therefore, it is unnecessary to make cumbersome selecting operation for selecting the important test items one by one, improving the operability. Furthermore, displaying only important test items reduces unnecessary information, making it easy to observe the test values of the important test items and the treatment records. This may prevent diagnostic errors based on a mistake in reading the test values.

Moreover, the representative case graph 73 is displayed on the basis of the representative case information 51 along with the test value graph 72 on the subject patient under medical practices in a manner allowing comparison therebetween, which is very useful for deciding on the therapeutic strategy or examining the therapeutic effect. As for the representative case information 51, test values and treatment records are extracted with respect to the obtained important test items, it is unnecessary to make cumbersome selecting operation for selecting the important test items one by one, improving the operability. Furthermore, displaying only important test items reduces unnecessary information, making it easy to observe the test values and the treatment records.

Displaying the test value graph 72rm and the representative case graph 73 in a superposed manner or an apposed manner facilitates comparison therebetween. Furthermore, displaying the treatment records in addition to the test values helps planning the therapeutic strategy.

Since the representative case information 51 is selectable from the case list 66, it is easy to select necessary representative case information. As the representative case information 51 is classified according to severity on each injury or disease, a comparison with a suitable representative case is available.

Second Embodiment

Next, a second embodiment of the present invention will be described. The second embodiment is configured to have a capability of informing such representative case information 51 that has been selected by other users with respect to the same injury or disease in addition to the configuration of the first embodiment. The informing function utilizes the input histories 56 stored in the storage device 33S shown in FIG. 4, as recited in the first embodiment. Note that, in the present embodiment, the same components will be designated by the same reference numerals as in the first embodiment, so that the detailed description thereof will be omitted.

As shown in FIG. 11, date information obtained at the time of selecting the representative case information 51, a user ID, an injury/disease code and a case ID are recorded as the input history 56 in correlation with each other. The date information represents the date and time when the representative case information 51 was selected. The user ID is user identifying information for identifying the user who has selected the representative case information 51. The injury/disease code recorded in the input history 56 is that was used for retrieval of the representative case information 51, that is, included in the delivery request which has been sent from the department terminal 16. The case ID is information for identifying each case of the representative case information 51.

The server controller 42 functions also as the informing section of the present invention, which causes the display 38 of the department terminal 16 to display a recommended case information screen 90, as shown in FIG. 12, when the server controller 42 delivers the case list 66 to the department terminal 16 to accept a selection from the representative case information 51. The recommended case information screen 90 displays a recommendation list 91 of those cases selected by other users from among the representative case information 51 with respect to the same injury or disease. On the recommendation list 91, one of the cases can be selected with the mouse pointer 63 by operating the input device 39. When a content display button 92 is clicked on by the mouse pointer 63, the contents of the selected case of the representative case information 51 are displayed on the display 38. After confirming the contents, an enter button 93 is clicked on to use the selected case of the representative case information 51. Then, case selecting information is transmitted from the department terminal 16 to the server controller 42.

Figure 13:
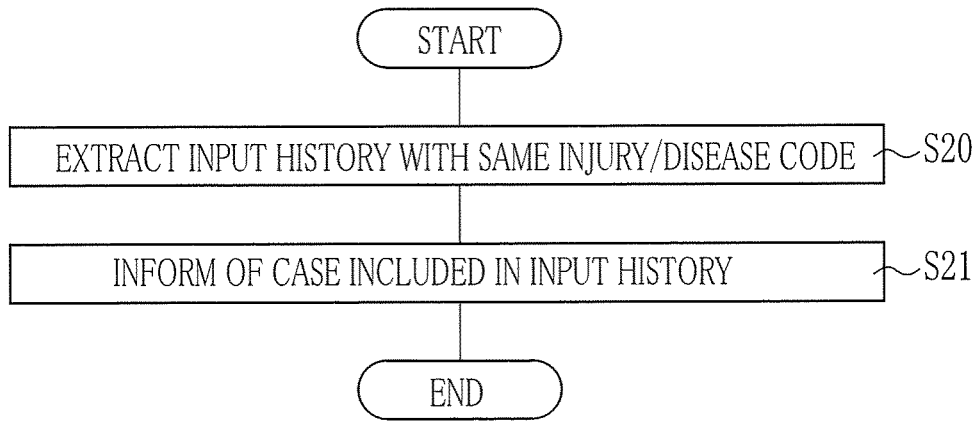
FIG. 13 is a flowchart illustrating a sequence of procedures for displaying the recommended medical case noticing screen.

The recommendation about the representative case information 51 on the recommended case information screen 90 is performed in a procedure shown in the flowchart of FIG. 13. The server controller 42 extracts an input history with the same injury/disease code as that included in the delivery request from among the input histories 56 (S20), and informs the department terminal 16 of a recommendation list 91 by means of the recommended case information screen 90, the recommendation list 91 indicating representative cases that correspond to the case ID included in the extracted input history (S21). The present embodiment makes it possible to recommend proven information on representative cases that have been actually utilized in the medical field.

Third Embodiment

Next, a third embodiment of the present invention will be described. The third embodiment relates to a function for registering new representative information 51 while utilizing the case registration unit 47 and the past case information 51, which have been described in the first embodiment and are shown in FIG. 4. Note that, in the present embodiment, the same components will be designated by the same reference numerals as in the first embodiment, so that the detailed description thereof will be omitted.

Figure 14:
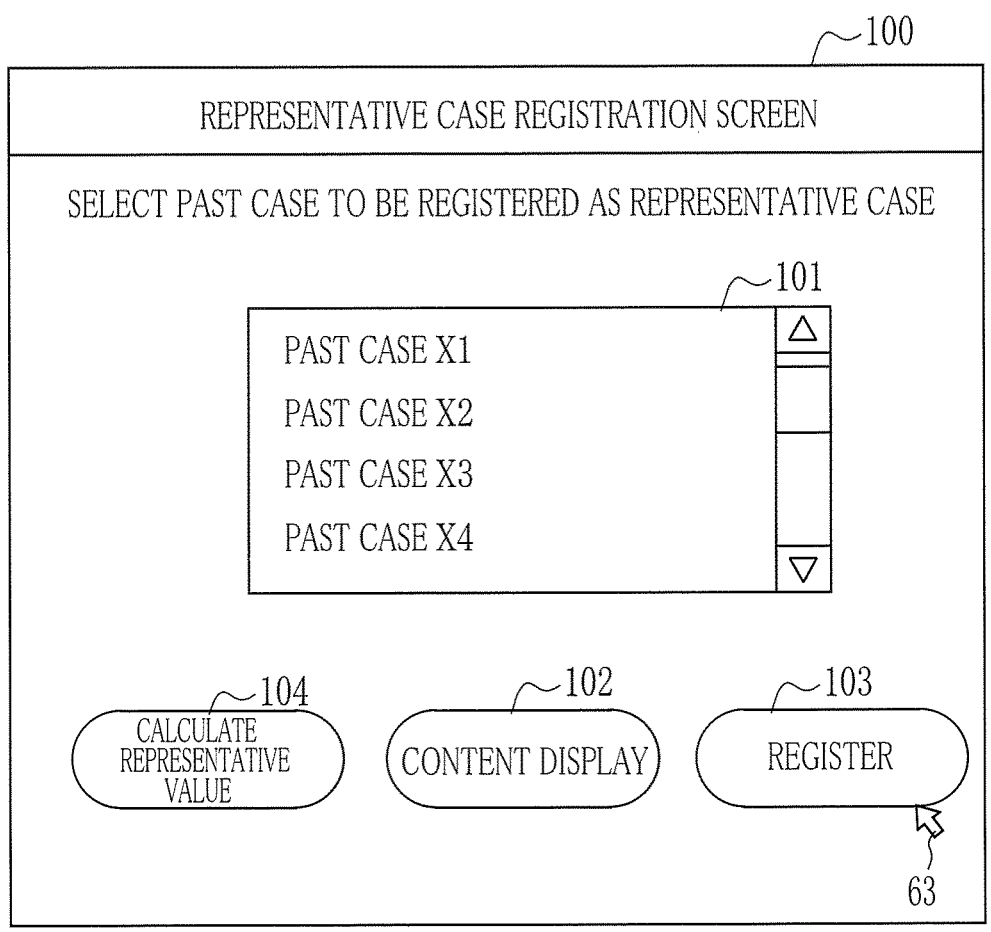
FIG. 14 is an explanatory diagram illustrating an example of a representative case registration screen.

When the input device 39 is operated to input an injury/disease name as a subject for which a new representative case is to be registered, the terminal controller 41 of the department terminal 16 accepts the input of the injury/disease name, and transmits a case registration request, including an injury/disease code of the input injury/disease name, to the integration server 15. The server controller 42 of the integration server 15 controls the case registration unit 47 to start registering new representative case information on the basis of the case registration request. Then, the DB access unit 43, which serves also as the past case obtaining section of the present invention, reads out those past cases corresponding to the injury/disease code of the case registration request from among the past case information 51 stored in the case DB 15a, and sends information on the read past cases to the department terminal 16. Then, the terminal controller 41 controls the display 38 to display a representative case registration screen 100, as shown in FIG. 14.

The representative case registration screen 100 is provided with a past case list 101 indicating the read past cases, a contents display button 102 for checking the contents of the past cases on the list, a registration button 103 operated to register any of the past cases as a representative case, and a representative value calculation button 104. By operating the representative value calculation button 104, the case registration unit 47 calculates representative values on the basis of test values contained in some past cases on the past case list 101, and the calculated representative values can be registered as representative case information 51. For example, averages, mean values or intermediate values of the test values included in the past cases are calculated as the representative values. The buttons 102 to 104 may be clicked on by the pointer 63 that is operated through the input device 39 of the department terminal 16.

Figure 15:
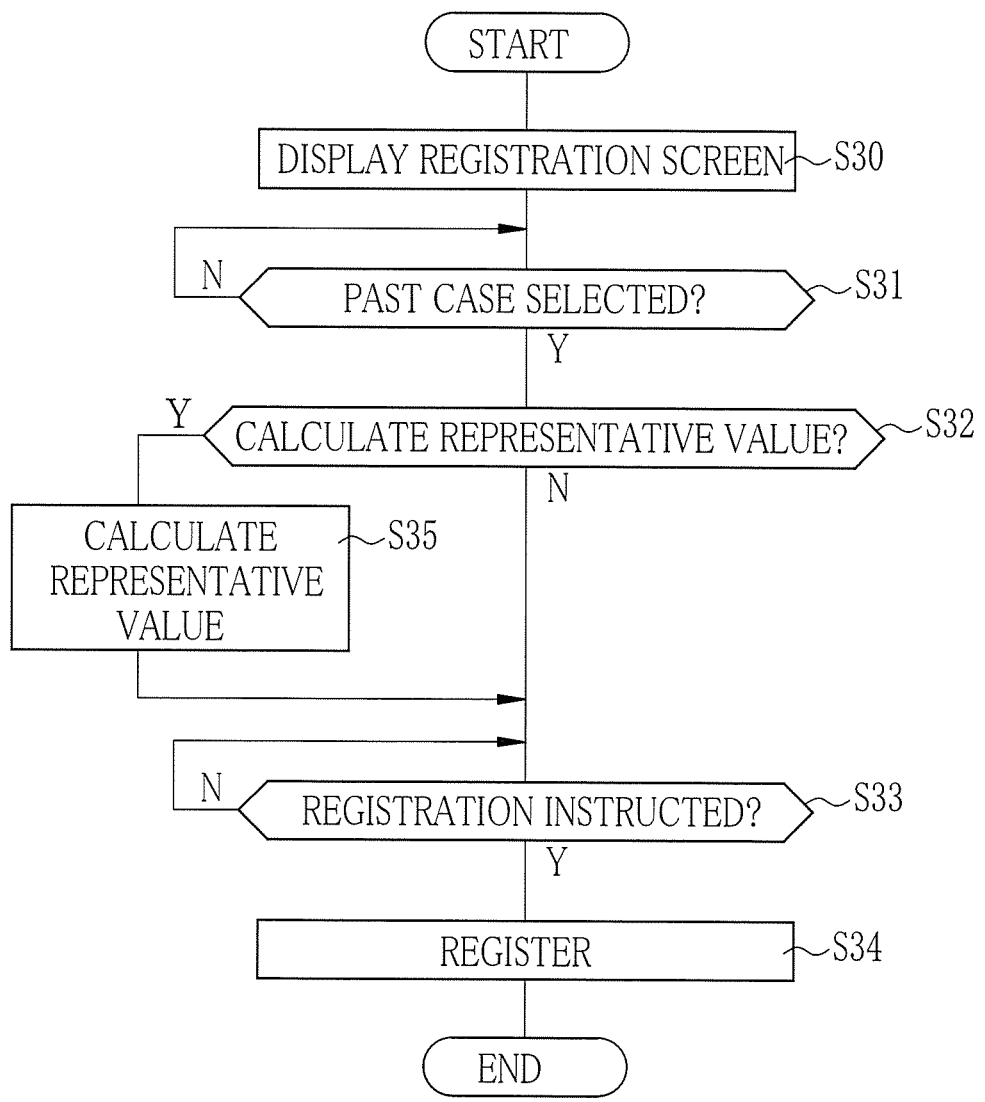
FIG. 15 is a flowchart illustrating a sequence of procedures for registering a representative case.

The registration of a representative case is made in a procedure shown in the flowchart of FIG. 15. As described above, the representative case registration screen 100 is displayed on the display 38 of the department terminal 16 (S30). By operating the input device 39 of the department terminal 16, one of the past cases on the past case list 101 is selected by the mouse pointer 63 (YES in S31). When the contents display button 102 is clicked on, the contents of the selected past case are displayed on the display 38. To register the past case as a representative case, after checking the contents thereof, the registration button 103 is clicked on (NO in S32 and YES in S33). Thus, information on the selected past case is registered as new representative case information 51 (S34).

If the representative value calculation button 104 is clicked on (YES in S32) after multiple past cases are selected (YES in S32), the case registration unit 47 calculates representative values of the test values contained in these past cases (S35). Thereafter when the registration button 103 is clicked on (YES in S33), the calculated representative values are registered as representative case information 51 (S34). Note that it may be possible to designate the severity when registering the representative case information 51 on the basis of the past case information 51. Designation of the severity may be done by the user, or the case registration unit 47 may automatically determine the severity on the basis of the test values and the like.

According to the present embodiment, the representative case information 51 is created on the basis of the past case information 52 on multiple cases of actually performed medical practices, so that it is possible to create representative case information suitable for actual medical practices. Furthermore, due to the capability of selecting a suitable case for a representative case from among the past case information 51 on multiple past cases, a high quality of the registered representative case information 51 will be achieved. Moreover, it is also possible to create the representative case information 51 from those past cases which accord to the trend of medical practices in each medical facility, so that the efficiency of medical practices can be improved in each medical facility.

Note that the past case information 51 may be stored in the case DB 15a in a manner classified according to the severity, so that the representative case information 51 may be registered while classified according the severity. That is, when registering a representative case, multiple cases are read out of the past case information 51 according to the severity, and the object to be registered is selected from among the read past case information 52.

To classify the past case information 51 according to the severity, it is possible to employ common methods for classification of the individual kinds of injuries and diseases. For example, the "JRS Guidelines for the Management of Community-Acquired Pneumonia in Adults" for determination on the severity of pneumonia, the "TNM Classification" for determination on the severity of cancer, the "NYHA Functional Classification" for determination on the severity of cardiovascular disease, the "AHA/ACC Stage Classification", etc. are applicable. Thus, registration of optimum representative cases according to severities thereof will be achieved. As it is unnecessary for the user to determine the severity of each case in the past case information 51 when registering the representative case information 51, it becomes easy to register the representative case information 51 according to the severity. Alternatively, it is possible to classify the past case information 51 according to the severity designated by the user when reading the past case information 51 from the case DB 15a.

In addition, it is possible to input manually test values and injury/disease names of those cases which are described in published documents or articles on medical examinations in order to register the representative case information 51. The test values recited in the publications are general or ordinary values and therefore may be regarded as suitable test values for representative medical cases. Providing these functions makes it easy to register those medical cases which involve suitable test values for representative cases.

Fourth Embodiment

Next, a fourth embodiment of the present invention will be described. The fourth embodiment relates to a capability of narrowing down the representative case information 51 when retrieving the representative case information 51 from the case DB 15a. Note that, in the present embodiment, the same components will be designated by the same reference numerals as in the first embodiment, so that the detailed description thereof will be omitted.

Figure 16:
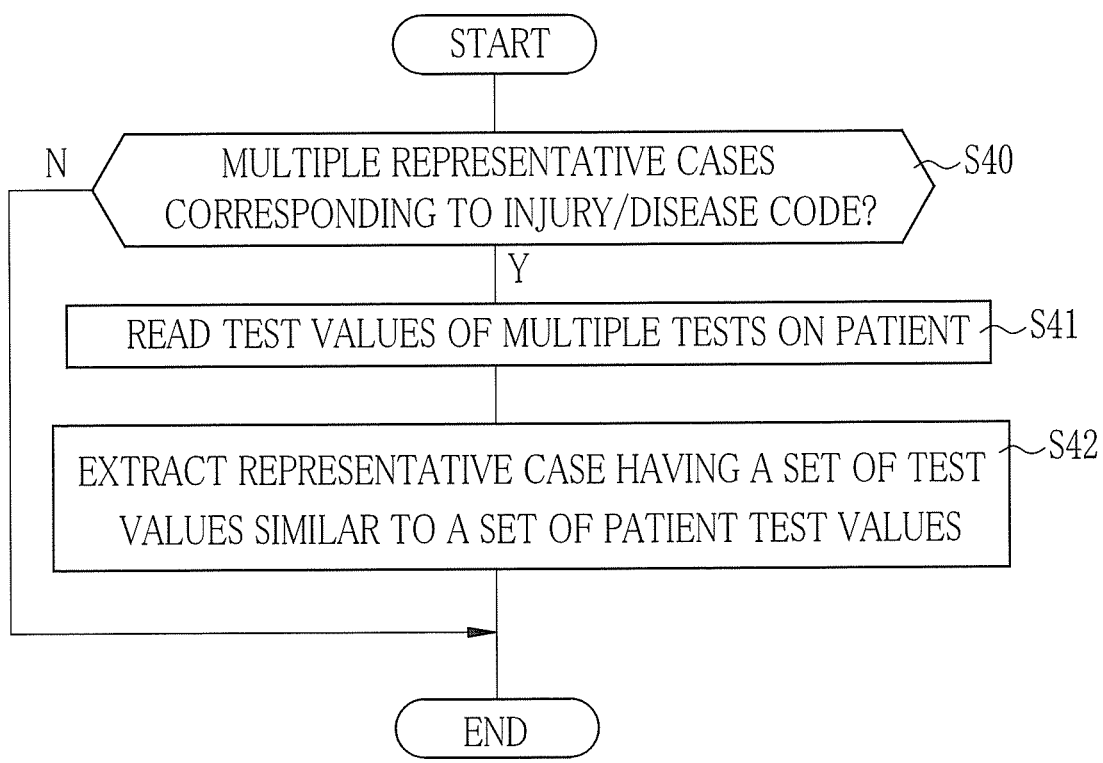
FIG. 16 is a flowchart illustrating a sequence of procedures for narrowing down the representative case information.

The narrowing down of the retrieved representative information 51 is performed in a procedure shown in the flowchart of FIG. 16. When multiple cases of the representative information 51 are retrieved (YES in S40), the case list creation unit 46, which functions also as the extracting section of the present invention, reads out test values of multiple medical tests on the important test items from the medical information 32 (S41). The case list creation unit 46 extracts, from among the multiple cases of representative information 51, one having a set of test values that are similar to the set of the read test values of multiple tests on the patient (S42). Alternatively, it is possible to display the retrieved multiple cases of representative information 51 in a manner ranked according to the similarity to the test values on the patient.

According to the present embodiment, it is possible to narrow down the representative case information 51 that includes multiple cases, so that even unexperienced doctors can select the representative case information 51 without hesitation. Furthermore, since the narrowing is based on the similarity to the test values of the patient, it is possible to extract such a representative case that is similar in severity to the case of the patient even while the representative case information 51 is not classified according to the severity.

Fifth Embodiment

Next, a fifth embodiment of the present invention will be described. Note that, in the fifth embodiment, the same components will be designated by the same reference numerals as in the first embodiment, so that the detailed description thereof will be omitted. The fifth embodiment is configured such that the user (like a doctor) can manually input an injury/disease name or an injury/disease code as a key word for retrieval of important test items, instead of obtaining automatically from the medical information 32.

As described with respect to the first embodiment, in general, an injury/disease name and an injury/disease code are often changed to a receipt name and an injury/disease code corresponding to the receipt name when recorded as medical information in an electronic medical record. The first embodiment has been described on the premise that the injury/disease name is not changed to the receipt name in the medical information 32, but in a case where the injury/disease name is changed to the receipt name in the medical information 32, the following problem could occur: the comparative display screen 71 would be produced on the basis of an injury/disease code which correspond to the receipt name, and the consequent comparative display screen 71 would display test values of those important test items which correspond to the receipt name and the corresponding representative case information. In that case, if the receipt name is not so largely changed from the injury/disease name that the doctor has diagnosed, no problem could occur. However, if the receipt name is largely changed from the original injury/disease name, the test values and the representative case information 51 on the comparative display screen 71 would differ from what the user doctor intends to browse. Then, the comparative display screen 71 cannot provide the expected function.

Figure 17:
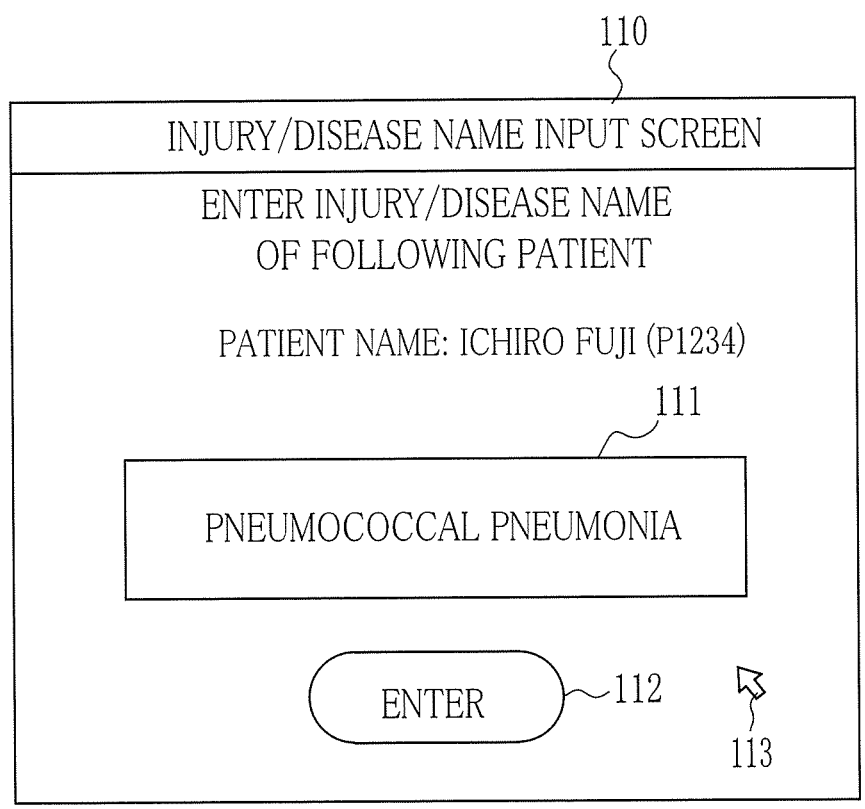
FIG. 17 is an explanatory diagram illustrating an example of an injury/disease name input screen.
Figure 18:
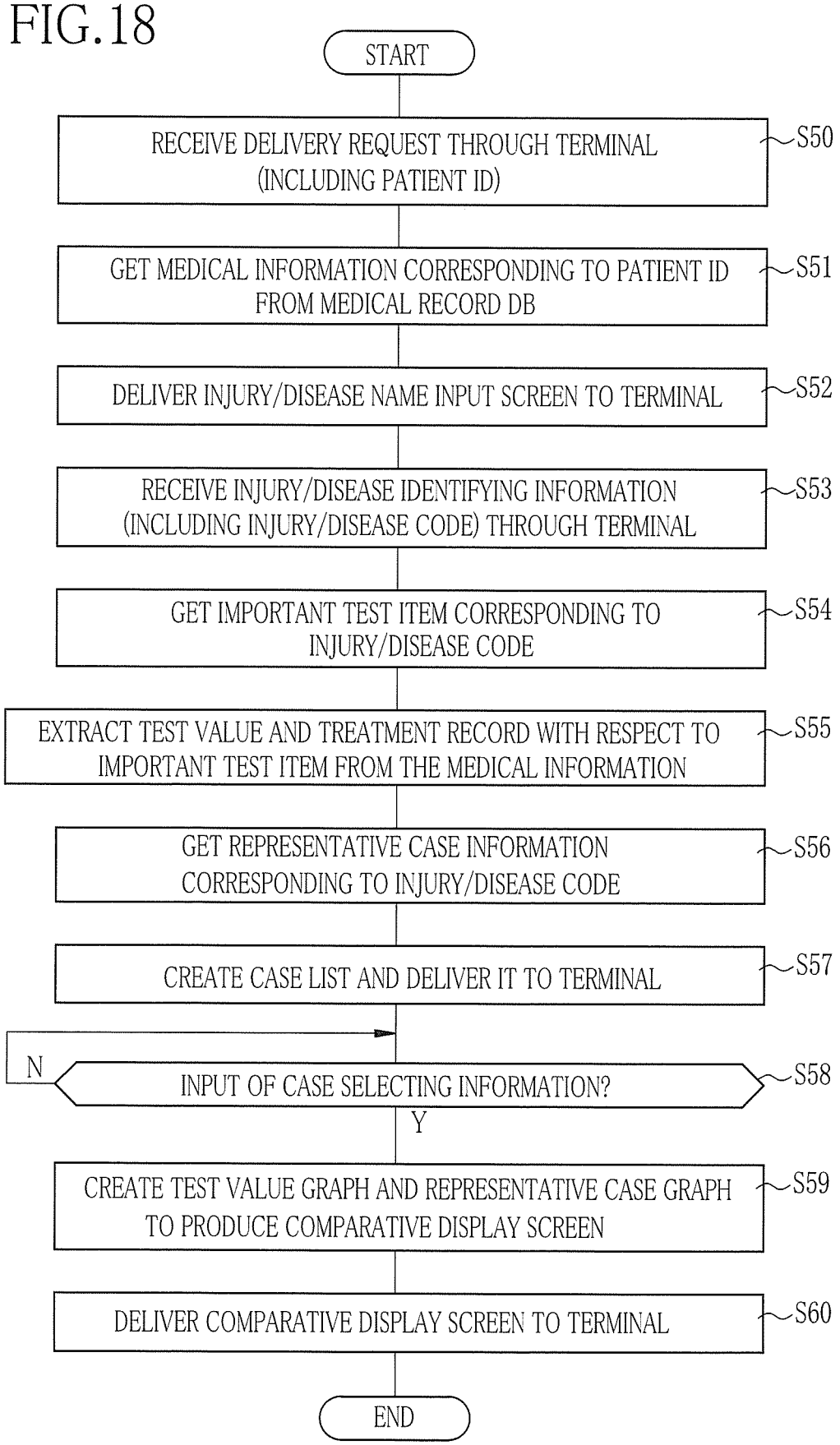
FIG. 18 is a flowchart illustrating a sequence of procedures for displaying a comparative display screen on the basis of an injury/disease name entered through an injury/disease name input screen.

In the present embodiment, in order to solve the above problem, an injury/disease name input screen 110 as shown in FIG. 17 is displayed on the display 38 of the department terminal 16, so as to accept an input of an injury/disease name by the user when the user instructs the display of the comparative display screen 71. Specifically, as shown in FIG. 18, when the terminal controller 41 of the department terminal 16 accepts an input of the display command for the comparative display screen 71 on the medical record display screen 61, the terminal controller 41 reads out a patient ID from the medical information 32 displayed on the medical record display screen 61 and sends a delivery request including the read patient ID to the integration server 15. The integration server 15 receives the delivery request from the department terminal 16 (S50).

In the integration server 15, the DB access unit 43 obtains the medical information 32 from the medical record DB 11a in correspondence with the patient ID included in the delivery request (S51). The screen production unit 44 transmits the injury/disease input screen 110 to the department terminal 16 (S52). The terminal controller 41 controls the display 38 to display the injury/disease input screen 110.

The injury/disease input screen 110 is provided with an entry field 111 for inputting an injury/disease name through the input device 39 and an enter button 112 for entering and sending the input injury/disease name to the integration server 15. In addition, the patient name, the patient ID and a message prompting the user to input an injury/disease name in the entry field 111 are displayed above the entry field 111. When the injury/disease name is input in the entry field 111 and the enter button 112 is clicked on by a mouse pointer 113, the terminal controller 41 sends injury/disease identifying information that includes an injury/disease name code corresponding to the input injury/disease name to the integration server 15. The injury/disease name may be input in the entry field 111 through the keyboard, or a list of injury/disease names may be displayed upon the entry field 111 being clicked on by the mouse. Note that the terminal controller 41 preferably stores data on correlation between injury/disease names and injury/disease codes in a storage device 33, so as to determine an injury/disease code on the basis of the injury/disease name.

Upon receipt of the injury/disease identifying information from the department terminal 16 (S53), the server controller 42 accesses the storage device 33S to refer to the important test item information 54 and obtain important test items corresponding to the injury/disease code included in the injury/disease identifying information (S54). Then, from among the test values of a plurality of test items included in the medical information 32, the server controller 42 extracts test values of the obtained important test items (S55).

The case list creation unit 46 retrieves the representative case information 51 on multiple cases of different severities from the case DB 15a on the basis of the injury/disease code (S56), and creates and sends a case list 66 to the department terminal 16 (S57). The terminal controller 41 controls the display 38 to display the delivered case list 66, thereby to accept a selection of the representative case information 51. When a case is selected from among the representative case information 51, the case selecting information is sent to the server controller 42 (YES in S58). The screen production unit 44 produces a comparative display screen 71 on the basis of the test values on the patient with respect to the extracted test items and the representative case information 51 designated by the case selecting information (S59), and delivers the produced comparative display screen 71 to the department terminal 16 (S60). Thus, the comparative display screen 71 is displayed on the display 38. Note that the above steps S54 to S60 are equivalent to the steps S12 to S18 in the first embodiment, respectively, the detail of these steps will be omitted.

As describes so far, the present embodiment enables the user to name the injury/disease to be displayed on the test value graph 72, allowing to browse a comparative display screen 71 regarding the injury/disease expected by the user, even while the medical information 32 records receipt names.

Although the present embodiment is configured to enter the injury/disease name by means of the injury/disease input screen 110, it is possible to configure a test result display device that is provided, for example, with the automatic injury/disease code obtaining function in accordance with the first embodiment, and the injury/disease name entering function in accordance with the present embodiment as well, such that the automatic injury/disease code obtaining function and the injury/disease name entering function can be switched over upon selection by the user, or depending on whether the injury/disease names recorded in the medical information 32 are receipt names or not.

Although the test result display devices 14 of the above embodiments are each constituted of the integration server 15 and the department terminal 16, a test result display device may be configured only by a department terminal 16 if the department terminal 16 is provided with the function of the integration server 15. Furthermore, instead of registering the representative case information 51 on the basis of the past case information 51 on multiple cases stored in the case DB 15a, it is possible to register the representative case information 51 on the basis of the test results in the medical information 32 stored in the medical record DB 11a.

The above embodiments have been described with respect to those examples where the department terminal 16 used for embodying the test result display device doubles as a terminal for electronic medical records, but it is possible to use a specific terminal which has no function as an electronic medical record terminal but has the test result display function only to embody the test result display device.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A medical test result display device, comprising:
  a non-transitory storage medium configured to store important test items for each injury or disease, wherein the important test items are test items, among multiple test items included in a medical test, that are considered important for each of the injury or disease, and test values of the important test items are expressed by numerical values;
  a processor configured to
  accept an input of an injury or disease identifying information to identify an injury or disease of a patient, wherein the patient is a present subject under a medical practice;
  read out important test items of the identified injury or disease from the non-transitory storage medium;
  access a test result storage to obtain medical information of the patient including test values of the patient corresponding to the important test items of the identified injury or disease;
  access a representative case storage to obtain a representative case information for use in comparison with the obtained test values of the patient, wherein the obtained representative case information includes test values of a representative medical case corresponding to the important test items of the identified injury or disease;
  produce a test value graph showing temporal change in the test values of the patient corresponding to the important test items of the identified injury or disease, wherein the temporal change in the test values of the patient corresponds to medical tests carried out on the patient a number of times at different time periods,
  produce a representative case graph showing temporal change in the test values of the representative medical case corresponding to the important test items of the identified injury or disease, wherein the temporal change in the test values of the representative medical case corresponds to a number of medical tests of the representative medical case carried out at different time periods,
  produce a comparative display screen comprising a first display field for displaying the test value graph and a second display field for displaying the representative case graph in a manner allowing comparison therebetween, wherein treatment records from the medical information of the patient other than the important test items are displayed in the first display field and treatment records from the representative case information other than the important test items are displayed in the second display field;
  create a case list of information on multiple representative cases stored in the representative case storage; and
  a display controller that controls displaying the comparative display screen on a display device,
  wherein the representative case storage stores representative case information classified according to the kinds and severities of injuries and diseases, and the representative case list shows representative case information on one injury or disease classified according to the severity,
  wherein the display controller displays the case list on the display device, and
  the processor accepts an input of case selecting information for selecting the representative case information to be displayed on the comparative display screen from the case list.

2. The medical test result display device set forth in claim 1, wherein
  the test value graph of the patient and the representative case graph are displayed on the comparative display screen a manner superposed on each other or in a manner apposed on each other.

3. The medical test result display device set forth in claim 1, wherein
  the representative case info illation includes records of medical treatments performed in the representative medical case in addition to the test values of the representative medical cases, and the comparative display screen displays the records of medical treatment in addition to the representative case graph.

4. The medical test result display device set forth in claim 1, wherein
  the non-transitory storage medium is further configured to store input history information of individual users, which associates an input history of the injury or disease identifying information with an input history of the case selecting information; and
  based on the input history information, the processor informs the user of the representative case information that other users have selected with respect to the same injury or disease.

5. The medical test result display device set forth in claim 1, wherein
  the processor is further configured to register representative cases in the representative case storage.

6. The medical test result display device set forth in claim 5, wherein
  the processor is further configured to access a past case storage to obtain past case information, the past case storage stores past case information on multiple cases, indicating test values of past medical tests carried out on other patients than the patient as the present subject of the medical practice, wherein the processor registers representative case information on the basis of the past case information obtained from the past case storage.

7. The medical test result display device set forth in claim 6, wherein
the processor registers past case information selected from the past case information obtained from the past case storage as representative case information.

8. The medical test result display device set forth in claim 6, wherein
the processor calculates representative values on the basis of test values included in the past case information on multiple cases, and registers the calculated representative value as representative case information.

9. The medical test result display device set forth in claim 6, wherein
the past case storage stores the past case information classified according to the kinds and severities of injuries and diseases, and the processor registers representative case information classified according to the kinds and severities of injuries and diseases on the basis of the past case information.

10. The medical test result display device set forth in claim 6, wherein
the processor is capable of receiving representative case information entered through a manual operation.

11. The medical test result display device set forth in claim 1, wherein
the representative case information obtained by the processor includes multiple representative medical cases, and the processor is further configured to extract, from the multiple representative medical cases, a representative medical case that contains a set of test values having temporal change which corresponds to the temporal change in the test values of the patient.

12. A method for operating a medical test result display device for displaying test results of medical tests, comprising:
a receiving step to accept an input of an injury or disease identifying information to identify an injury or disease of a patient, wherein the patient is a present subject under a medical practice;
an important test item reading step to read out important test items of the identified injury or disease, which correspond to the injury or disease identifying information received in the receiving step, from a non-transitory storage medium which stores important test items for different kinds of injury or disease, wherein the important test items are test items, among multiple test items included in a medical test, that are considered important for each injury or disease, and the test values of the important test items are expressed by numerical values;
a test result obtaining step to obtain medical information of the patient including test values of the patient corresponding to the important test items of the identified injury or disease and to obtain a representative case information for use in comparison with the obtained test values of the patient, wherein the obtained representative case information includes test values of a representative medical case corresponding to the important test items of the identified injury or disease,
a screen producing step to produce a test value graph showing temporal change in the test values of the patient corresponding to the important test items of the identified injury or disease, a representative case graph showing temporal change in the test values of the representative medical case corresponding to the important test items of the identified injury or disease, and a comparative display screen comprising a first display field for displaying the test value graph and a second display field for displaying the representative case graph in a manner allowing comparison therebetween, wherein treatment records from the medical information of the patient other than the important test items are displayed in the first display field and treatment records from the representative case information other than the important test items are displayed in the second display field, wherein the temporal change in the test values of the patient corresponds to medical tests carried out on the patient a number of times at different time periods, and the temporal change in the test values of the representative medical case corresponds to a number of medical tests of the representative medical case carried out at different time periods, and
a display control step to control displaying the comparative display screen on a display device,
wherein a case list of information is created on multiple representative cases, the representative case information is classified according to the kinds and severities of injuries and diseases, and the representative case list shows representative case information on one injury or disease classified according to the severity,
wherein the display control step is further controlled to display the case list on the display device, and the receiving step further accepts an input of case selecting information for selecting the representative case information to be displayed on the comparative display screen from the case list.

* * * * *